(12) United States Patent
Mondet et al.

(10) Patent No.: US 6,352,699 B1
(45) Date of Patent: Mar. 5, 2002

(54) COSMETIC OR DERMATOLOGICAL COMPOSITION FORMING, ON A KERATIN SUBSTRATE, A FILM IN CROSS-LINKED HYBRID MATERIAL

(75) Inventors: Jean Mondet, Aulnay-sous-Bois; Francis Xavier Quinn, Paris; Clément Sanchez, Gif-sur-Yvette, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/381,735

(22) PCT Filed: Apr. 3, 1997

(86) PCT No.: PCT/FR98/00682

§ 371 Date: Dec. 3, 1999

§ 102(e) Date: Dec. 3, 1999

(87) PCT Pub. No.: WO98/44906

PCT Pub. Date: Oct. 15, 1998

(30) Foreign Application Priority Data

Apr. 4, 1997 (FR) .............................. 97 04157

(51) Int. Cl.$^7$ ................................. A61K 7/00
(52) U.S. Cl. ................... 424/401; 424/61; 424/63; 424/70.1; 424/70.12
(58) Field of Search ............... 424/61, 63, 70.1–70.12, 424/401

(56) References Cited

U.S. PATENT DOCUMENTS

| 4,921,942 A | 5/1990 | Bernhardt et al. ............. 424/59 |
| 5,599,530 A | * 2/1997 | Patil et al. ..................... 424/63 |

FOREIGN PATENT DOCUMENTS

| EP | 0 113 992 | 7/1984 |
| EP | 0 117 360 | 9/1984 |
| EP | 0 220 934 | 5/1987 |
| EP | 0 277 244 | 8/1988 |
| EP | 0 281 034 | 9/1988 |
| WO | WO 94 07947 | 4/1994 |

* cited by examiner

Primary Examiner—Jose' G. Dees
Assistant Examiner—Konata M. George
(74) Attorney, Agent, or Firm—Nixon & Vanderhye P.C.

(57) ABSTRACT

The invention concerns a cosmetic or dermatological composition designed for for forming a film on a keratin substrate, in cross-linked hybrid material. Said composition is of the sol/gel type and is obtained by mixing: (a) at least an organometallic compound; (b) at least a functionalised organic polymer or said polymer precursor, or at least a functionalised silicone polymer or said polymer precursor, the precursor being different from (a); (c) a sufficient amount of water for hydrolysing the organometallic compound: and (d) optionally at least an alcohol; said film being non-reversible.

25 Claims, No Drawings

COSMETIC OR DERMATOLOGICAL COMPOSITION FORMING, ON A KERATIN SUBSTRATE, A FILM IN CROSS-LINKED HYBRID MATERIAL

The present invention relates to a cosmetic or dermatological composition forming a film-forming coating of a crosslinked hybrid material on a keratinous substrate after drying, and to its use, in particular in the field of hair products, make-up products and skincare products.

The expression "keratinous substrate" as used in the present invention means not only the hair, eyelashes, eyebrows and nails, but also the skin.

In the cosmetic and dermatological fields, a film is generally formed on a keratinous substrate using a variety of types of polymers in solution or as a dispersion. After drying, and depending on the nature of the polymer, films are obtained with mechanical and cosmetic characteristics which are specific to the envisaged use.

While until now a number of studies have been directed towards a wide variety of organic film-forming polymers primarily intended for haircare compositions or for nail varnish compositions, very few studies have been directed towards organic-inorganic polymers, also termed hybrid materials.

The first studies result from an article by F. Sardo, American Cosmetics and Perfumeries, vol. 87, 43–46 (1972) which describes, as a hair fixative, compositions containing organic titanate and dimethylsilicone copolymers, these being obtained by polymerizing a silicone and an organic titanate in the presence of water, and evaporating the alcohol formed. However, it was shown that such organic-inorganic copolymers had the disadvantage of being neither soluble nor dispersible in alcohols, in particular in ethanol. These proved only to be soluble in non-cosmetic solvents such as aliphatic, aromatic and chlorinated hydrocarbons, in particular in 1,1,1-trichloroethane. That article also indicates that the major disadvantage of such organic-inorganic polymers is that they cannot be eliminated, even after several washes, because of their high adhesion to the hair.

U.S. Pat. No. 4,344,763 also describes a hair shaping method consisting in moistening the hair with water then applying a solution containing, in isopropanol, 0.5% to 15% by weight of an aminoalkylalkoxysilane and 0.005% to 1.5% by weight of an organic titanate and then shaping the hair as desired. In that method, it is particularly recommended that the isopropanol solution be kept protected from any moisture.

Further, in contrast to the article by F. Sardo, it is maintained that that method only leads to temporary shaping of the hair and thus is reversible in nature.

EP-A-0 113 992 also describes a method for simultaneously fixing and conditioning the hair using a composition, which is stable in the absence of moisture, containing (A) a siloxane oligomer containing at least one nitrogen-hydrogen bond and (B) a readily hydrolysable anhydrous additive selected from titanates, zirconates, vanadates, germanates and mixtures thereof.

As in the article by F. Sardo, the solvent for the composition is an aliphatic hydrocarbon or an aliphatic halohydrocarbon, preferably 1,1,1-trichloroethane. After applying the composition to the hair, the hair is placed in a moist atmosphere to cause crosslinking of the siloxane oligomer and the readily hydrolysable anhydrous additive. The crosslinked film formed on the hair is described in that patent as also being reversible, i.e., that after washing, even with water, the hair loses its initial shape, this phenomenon of reversibility being assumed to be due to de-cross-linking.

An analysis of the prior art leads to the conclusion that no valid solution has been proposed for forming, by an easily implemented method, a film of a hybrid material of a non reversible nature by an in situ sol/gel reaction, from a stable cosmetic or dermatological composition which is easy to apply.

In certain cosmetic applications, in particular in the treatment of hair, and more particularly in the treatment of nails, it is important to be able to produce a film with good adhesive properties which can withstand over time a large number of washes without its properties being affected.

Thus one aim of the present invention is to provide a composition for fixing and/or colouring the hair which can, in a single application after rapid drying, produce long-lasting hold and/or coloration which can withstand washing, even after several shampoos, without affecting the properties endowed upon the hair.

A further aim of the present invention is to provide an eyelash make-up composition such as a mascara which, after drying, produces good coverage and coloration of the eyelashes while being resistant to water and to ambient humidity.

A further aim of the present invention is to provide a colourless or coloured nail varnish composition giving rise to a film with excellent gloss, good surface hardness, good mechanical properties, in particular impact strength (no flaking) and which can withstand washing with water, detergents and other normal organic cosmetic solvents.

Finally, a further aim of the present invention is to provide a composition for skin care or treatment to endow it with a care and protective effect giving rise to an invisible film which can withstand dry rubbing, washing and detergents.

The subject of the present invention is thus a cosmetic or dermatological composition for forming a coating of a crosslinked hybrid material on a keratinous substrate, characterized in that said composition is a sol/gel type composition and is obtained by mixing:
  (a) at least one organometallic (or metallo-organic) compound;
  (b) at least one functionalized organic polymer or a precursor of said polymer, or at least one functionalized silicone polymer or a precursor of said polymer, the latter precursor being different from (a);
  (c) a sufficient quantity of water to hydrolyse the organometallic compound; and
  (d) optionally, at least one alcohol; said coating being non reversible in nature.

The expression "functionalized" as used in the invention means the presence of functional groups which can interact physically or chemically.

The expression "non reversible" as used in the invention means that the hybrid material formed after application of the composition and evaporation of the solvent(s) retains its initial structure, i.e., it is not de-crosslinked after several washes with water.

This non-reversibility of the hybrid material formed in accordance with the invention is essentially due to the fact that it has a high degree of cross-linking on a nanometric scale and a very low surface energy.

When the composition as defined above is applied to a keratinous substrate, a sol/gel reaction occurs which, after evaporation of the solvent(s), leads to the formation of a hybrid material by polycondensation and cross-linking on a nanometric scale.

The crosslinked hybrid material thus formed can be of a highly varied structure. It can thus be in the form of a more or less dense network of inorganic polymer chains originating from the organometallic compound and chains of organic or silicone polymer, these being connected together by physical, ionic and/or covalent bonds.

The hybrid material can also consist of mineral nodules originating from the organometallic compound and chains of organic or silicone polymer, the nodules being physically or chemically linked to the organic or silicone polymer chains. The nanometric size of the mineral nodules is very small, generally in the range 1 to 20 nanometers. These nodules can also take the form of aggregates or clusters.

The organometallic compound of the sol/gel type composition of the invention can be selected from the group formed by:
  (i) oxides of transition metals from groups 1b to 7b, from group 8 or from the lanthanide series in the periodic table;
  (ii) aluminium, boron, silicon, tin, titanium, cerium or tungsten oxides; and
  (iii) aluminium phosphates.

Preferably, the organometallic compound is selected from the group formed by:
  (1) alkylsilanes, alkyl titanates or alkyl zirconates corresponding to one of the following formulae:

 (Ia)

 (Ib)

 (Ic)

(Id)

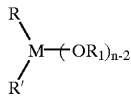

where:
  m represents Si, Ti or Zr;
  n represents the valency of the metal;
  $R_1$ represents a linear or branched $C_1$–$C_{30}$, preferably $C_1$–$C_6$, alkyl radical;
  R and R', independently of each other, represent a linear or branched alkyl radical, a cycloalkyl radical, a substituted or unsubstituted aryl radical, said radicals R and R' possibly being substituted by groups which are capable of reacting with the organic or silicone polymer, such as, for example, ethylenically unsaturated groups ((meth)acrylic, vinylic, . . . ), halogenated groups, hydroxylated groups, carboxylated groups, thiol groups, epoxy groups, ester groups, urethane groups, urea groups, amine groups, amino acid groups, polypeptide groups, etc., said radicals R and R' possibly also containing a cosmetically or dermatologically active group selected, for example, from a colorant group, a photochromic group, a UV-A and/or UV-B radiation filtering group, a group promoting adhesion to keratinous materials (amide groups, urethane groups, urea groups, hydroxyl groups, carboxyl groups, amino acid groups or polypeptide groups), a group facilitating make-up removal, a bactericidal group, a chelating group in particular one which can complex multivalent cations, a hydroxy acid, a neurosuppressant, a hair loss prevention group, an antioxidant group, a free radical scavenging group, or a vitamin carrying group; and (2) chelated alkylsilanes, alkyl titanates or alkyl zirconates corresponding to the following formula:

 (II)

where:
  M, $R_1$ and n have the same meanings as those given above for formulae (I);
  b represents the degree of complexation of the ligand X;
  x is the number of complexing ligands; and
  X represents a mono-or polydentate chelating ligand or group which can be covalently bonded to a group which can react with the organic or silicone polymer such as, for example, ethylenically unsaturated groups ((meth)acrylic, vinylic), halogenated groups, hydroxylated groups, carboxylated groups, thiol groups, epoxy groups, ester groups, amine groups, urea groups, urethane groups, the acetoacetate (ACAC) group or a group derived from EDTA and its derivatives, said chelating group possibly also comprising a cosmetically or dermatologically active group such as those defined above.

Of the compounds with formula (II) above, those with formulae (IIIa) to (IIId) below can more particularly be mentioned:

 (IIIa)

 (IIIb)

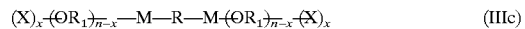 (IIIc)

(IIId)

where:
  M, X, R, R', $R_1$, n and x have the same meanings as those given above for formulae (I) and (II).

The chelating groups X can be selected from carboxylic acids, β-ketones, β-diketones, β-keto esters, β-keto amines, (α- and β-hydroxy acids, amino acids, preferably β-hydroxylated amino acids, salicylic acid and derivatives thereof. The following can be cited in particular: acetoacetoxyethyl methacrylate, methyl α-hydroxymethacrylate, ε-N-methacryloyl-L-lysine, 4- or 5-methacrylaminosalicylic acid.

Particularly preferred organometallic compounds of the invention which can be cited are tetraethoxysilane, tetraisopropyl orthotitanate, tetrapropyl zirconate, methyltriethoxysilane, titanium tetraethoxide, titanium tetrabutoxide, iron triethoxide and tungsten triethoxide.

The functionalized organic or silicone polymer of the sol/gel type composition of the invention can be a random, block and/or graft polymer, and is preferably selected from the group formed by:
  (a) homopolymers and copolymers of alkyloxazoline such as poly(2-ethyl-2-oxazoline);
  (b) homopolymers and copolymers resulting from copolymerization of (meth)acrylic acid, crotonic acid, maleic acid, itaconic acid, styrene-sulphonic acid, acrylamido-2-methyl-propane sulphonic acid, 2-sulphoethyl methacrylate, vinylsulphonic acid and vinylphosphonic acid;

(c) homopolymers of acrylic or methacrylic esters or amides and their copolymers with monomers selected from unsaturated carboxylic, sulphonic or phosphonic acids, vinyl esters or ethers, olefins, styrene, substituted styrenes such as hydroxystyrene, fluoro- or perfluoro-olefins, perfluoroalkyl (meth)acrylates, fluorinated vinyl compounds such as fluorinated vinyl ethers and unsaturated organosilanes, organosiloxanes or organopolysiloxanes;

(d) homopolymers and copolymers of vinyl alcohol;

(e) homopolymers of vinyl and/or allyl and/or methallyl esters or amides and their copolymers with monomers selected from unsaturated carboxylic, sulphonic or phosphonic acids, vinyl esters or ethers, olefins, styrene, substituted styrenes such as hydroxystyrene, fluoro- or perfluoro-olefins, perfluoroalkyl (meth) acrylates, fluorinated vinyl compounds such as fluorinated vinyl ethers and unsaturated organosilanes, organosiloxanes or organopolysiloxanes;

(f) polyethers such as homopolymers and copolymers of methylene oxide, ethylene oxide, propylene oxide or tetramethylene oxide;

(g) aromatic and/or aliphatic polyesters and polyesters obtained by opening of rings such as poly (caprolactone), polylactide, polyglycolide, and copolymers thereof;

(h) homo- and copolyolefins and homo- and copolycycloolefins such as polyethylenes, ethylene/vinyl acetate, ethylene/α-olefin, ethylene/cycloolefin, ethylene/(meth)acrylic: ester copolymers, and homo- and copolymers of polypropylene, polybutene, polyisobutene and polynorbornene;

(i) polyamides, polyesteramides and polyetheramides;

(j) polyurethanes and polyureas which may comprise polyether, polyester and/or polyorganosiloxane sequences, which may carry fluorinated groups;

(k) fluorinated polymers such as products sold by Ausimont under the trade name "Fomblin®" (perfluoropolyether);

(l) natural polymers and modified natural polymers such as ether and/or ester derivatives of cellulose or starch, polysaccharides, glycosaminoglycans and oligosaccharides, natural gums such as hydroxyalkylated guar gums for example hydroxypropylated guar gums, hydroxypropylated guar gums with carboxylic functions or quaternized, carob gum, xanthan gum, carrageenans, pectins, alginates, polypeptides or proteins such as collagen, elastin, gelatin or keratin;

(m) polyorganosiloxanes such as polydimethylsiloxanes, polymethylphenylsiloxanes, polyphenylsiloxanes, polyorganosiloxanes substituted laterally or at the chain end with amino acid groups, polyoxyethylene chains, amino or polyamino groups, hydroxyl groups, carboxylic acid groups, alkyl chains, vinyl or acrylic grafts or blocks, and fluorinated or perfluorinated grafts or blocks;

(n) polyorganophosphazines;

(o) polysilanes, polycarbosilanes or polysilazanes; and (p) mixtures thereof.

In one particular embodiment, the hydrocarbon homo- and copolymers such as those listed above can be blocked and/or grafted with polysiloxane chains.

The organic or silicone polymers can also comprise a cosmetically or dermatologically active group such as those listed above.

If, among the organic or silicone polymers listed above, certain are not functionalized, these can be functionalized either by reaction in the composition such as for example polyorganosiloxanes, or by prior reaction using the usual methods before formation of the composition.

The following particularly preferred organic or silicone polymers of the invention can be cited: poly(2-ethyl-2-oxazoline), the vinyl acetate/vinyl 4-tert-butylbenzoate/crotonic acid (65/25/10%) copolymer, polydimethylsiloxane-diols, polyethylene glycol, polyvinyl alcohol or polyvinylpyrrolidone.

The quantity of water present in the composition of the invention must, as indicated above, be such that it can permit hydrolysis of the organometallic compound. Its pH, which can be acidic or basic (1 to 12), will depend on the nature of the organometallic compound present in the composition.

Thus when the organometallic compound used is an alkyl titanate or an alkyl zirconate, the pH of the water is acidic, preferably 3 or less.

When present, the alcohol is preferably selected from linear or branched $C_1$–$C_6$ lower aliphatic alcohols such as ethanol or isopropanol.

In accordance with the invention, the weight ratio of the organometallic compound to the organic or silicone polymer is generally in the range from about 9:1 to 1:9, preferably in the range 8:2 to 2:8.

These ratios are relatively broad since, in certain cosmetic or dermatological applications, the mineral phase of the hybrid material must be preponderant with respect to the organic phase, or vice versa.

Thus when the composition is intended for hair care use to hold and/or colour the hair, the mineral phase of the hybrid material is generally in the range 10% to 99%, preferably in the range 20% to 75%.

In make-up products such as mascaras, the mineral phase is generally in the range 10% to 99%, preferably in the range 30% to 90%.

In colourless or coloured nail varnishes, the mineral phase of the hybrid material is generally in the range 50% to 99%, preferably in the range 60% to 90%.

Finally, when the composition is intended for application to the skin as an anti-wrinkle treatment, the mineral phase is generally in the range 5% to 99%, preferably in the range 10% to 70%.

When the composition of the invention contains a precursor of the organic or silicone polymer, it is essentially one or more monomers which can lead to a functionalized organic or silicone polymer by polymerization of unsaturated double bonds or by polycondensation during application of the composition.

Polymerization can be initiated conventionally by heating in the presence of conventional radical initiators, by irradiation with UV radiation, ionically (cationic or anionic) by electron beams or by any known polymerization method.

While this particular embodiment can be carried out in accordance with the invention, for practical reasons it is preferable to use a functionalized organic or silicone polymer which has already been produced.

In one particular embodiment of the invention, the composition can contain active cosmetic or dermatological ingredients which, during formation of the hybrid material, will be included in the matrix of said material. Examples of these different active ingredients which can be cited are colorants, coloured or colourless organic or mineral pigments, UV-A and/or UV-B sunscreens, enzymes, slimming agents, moisturizers, vitamins, α-hydroxy acids, etc.

Further, the compositions of the invention can also contain a variety of the usual cosmetic and dermatological additives, always provided that: these additives cannot interfere with the other constituents of the composition.

The composition of the invention as defined above can be used as a hair product in particular for holding or shaping. It can also colour the hair and/or protect it against the effects of UV radiation while endowing it with hold or fixing properties.

As described above, the crosslinked hybrid material, during formation, can include a variety of active ingredients such as organic or mineral pigments and/or UV filters.

The hair care composition is preferably in the form of a lotion for setting or blow-drying, or in the form of a gel. When the composition is in the form of a lotion, it can be packaged in a spray bottle, in a pump flask or in an aerosol container in the-presence of a usual propellent gas to obtain either a spray or a mousse.

The composition of the invention can also be used as a skin care, protection or treatment product, in particular as a long life antisun product as the coating of crosslinked hybrid material has good water and sea water resistance. In this embodiment, the crosslinked hybrid material contains, included, one or more UV filters.

The composition of the invention can also be an eye make-up product such as a mascara or eye-liner, or a nail product such as a coloured nail varnish to make up the nails, or a colourless nail base or nail care product.

When the composition is in the form of an eye make-up product or a coloured nail varnish, the organic and/or mineral pigments are also included in the crosslinked hybrid material.

A subject of the present invention is also the use of the composition of the invention in a hair treatment method to hold it and/or colour it.

In one embodiment of this method, a composition of the invention is applied to the hair, preferably in the form of a spray, either using a spray pump or using an aerosol. After spraying over the hair, the composition is allowed to act while the solvent(s) evaporate off, possibly then drying.

The hair can be shaped as desired either before application or immediately afterwards.

The drying time can vary and depends on the nature of the composition applied to the hair.

If deformation means are used, these are removed. After combing, the hair is shiny and wavy. Even after several washes using water and shampoo, the initial waviness of the hair is retained. This demonstrates the irreversible nature of the adhesion of the hybrid material to the hair surface.

When the composition contains at least one hair pigment and/or colorant, it can be included in the hybrid material during the sol/gel reaction on the hair such that the colour with which the hair is endowed is not modified by successive washes with water or using shampoo.

Another subject of the present invention is the use of the composition as defined above in an eyelash make-up method.

In this method, a sufficient quantity of the composition is applied using a mascara brush by carefully smoothing onto the eyelashes. After a drying time which varies depending on the composition, the eyelashes are shiny in appearance, the make-up having good resistance to water and to ambient humidity.

Another subject of the present invention is the use of the composition as defined above in a nail make-up or care method.

In this method, a thin layer of the composition of the invention is applied to the nail surface using a brush, the composition being coloured or colourless. The nails are allowed to dry for a time which varies depending on the nature of the composition and it is seen that the coating film deposited on the nails has excellent gloss and good surface hardness. Further, this film withstands washes with water, detergents and the usual organic solvents used in cosmetics. When the varnish composition of the invention contains at least one colorant and/or pigment, this can be included in the hybrid coating material so that no colour variation is observed over time even if the colouring substance is soluble in water or in the usual organic solvents.

Finally, a subject of the invention is the use of the composition as defined above in a method for treating or caring for the skin and in particular in an anti-wrinkle treatment method.

In this method, the composition of the invention is carefully applied to the parts of the skin where wrinkle reduction is desired, in particular around the eyes. The composition can be applied in a thin layer using any suitable means and, after evaporation of the solvent(s), leads to the formation of an invisible transparent film exerting a tightening effect which visually dissipates the wrinkles.

A number of examples of compositions of the invention and embodiments thereof will now be given by way of illustration.

EXAMPLES

Example 1

Nail Varnish

A nail varnish in accordance with the invention was produced by mixing the following ingredients:

| | |
|---|---|
| Tetraethoxysilane | 53.4% |
| Poly(2-ethyl-2-oxazoline) as a 50% solution in ethanol | 19.0% |
| Absolute ethanol | 11.8% |
| Water (pH = 1) | 9.2% |
| Iron oxide/propylene glycol (50/50) | 4.6% |
| Titanium oxide/propylene glycol (50/50) | 2.0% |

This nail varnish was produced by mixing the tetraethoxysilane in absolute ethanol and adding water brought to a pH of 1 (addition of hydrochloric acid).

After having allowed the reaction to continue for 30 minutes with stirring, the poly(2-ethyl-2-oxazoline) as a 50% solution in ethanol was added and stirring was continued for 15 minutes. Finally, the iron oxide in the propylene glycol was added and stirring was continued for 30 minutes and finally the titanium oxide in propylene glycol was added, continuing stirring for about 30 minutes.

A varnish was thus obtained which was easy to apply to the nail surface and after drying led to the formation of a homogeneous glossy film with excellent resistance to water, detergents and alcohol.

It also had excellent scratch resistance.

Example 2

Nail Varnish

A nail varnish in accordance with the invention was produced by mixing the following ingredients:

| | |
|---|---|
| Tetraisopropyl orthotitanate | 33.9% |
| Polydimethylsiloxanediol | 41.4% |
| Absolute ethanol | 18.3% |
| Water (pH = 1) | 0.4% |
| Iron oxide/propylene glycol (50/50) | 4.0% |
| Titanium oxide/propylene glycol (50/50) | 2% |

This nail varnish was produced using the same operating procedure as that described above in Example 1 and, on application to the nail surface, led to a glossy homogeneous film with excellent resistance to water, detergents and alcohol.

Example 3

Coloured Fixing Composition for Hair

This composition was prepared as follows:

10.4 g of diethoxydimethoxysilane were diluted in 4.6 g of ethanol and 0.6 g of water at a pH of 1 was then added (addition of hydrochloric acid). After stirring (about 1 minute), 14 g of tetrapropyl zirconate as a 70% solution in propanol were added, then 5.2 g of polydimethylsiloxanediol (average molecular weight=550). After stirring for 30 minutes, 0.15 g of Rhodamine 101 diluted in 1 g of ethanol was added. The dry extract of the solution was then brought to 25% by adding a volatile silicone oil (D5 from Dow Corning). 2.5 g of α-ω hydroxy/oxo silicone (viscosity 6500 cSt) from Dow Corning were then added.

The final solution obtained was then packaged in a suitable receptacle for spraying onto the hair.

After spraying and drying the hair, it was observed that the hair had a natural feel and was uniformly coloured and shiny.

Even after several washes with water or using a shampoo, the initial coloration of the hair persisted.

Example 4

Mascara

A composition in the form of a mascara was produced using the following ingredients:

| | |
|---|---|
| Tetraethoxysilane | 28.9% |
| Methyltriethoxysilane | 28.9% |
| Poly(2-ethyl-2-oxazoline) as a 50% solution in ethanol | 9.4% |
| Absolute ethanol | 13.9% |
| Water (pH = 1) | 9.45% |
| Iron oxide/propylene glycol (50/50) | 9.45% |

This mascara was obtained by mixing the tetraethoxysilane, methyltriethoxysilane and absolute ethanol to which water brought to a pH of 1 was then added (addition of hydrochloric acid). It was allowed to react for 30 minutes with stirring and then the poly(2-ethyl-2-oxazoline) as a 50% solution in ethanol was added and stirring was continued for about 15 minutes. The iron oxide in propylene glycol was then added and stirring was continued for 30 minutes. This mascara, by application to the eyelashes using a brush, produced a homogeneous, shiny and water resistant film after evaporation of the volatile components.

Example 5

Anti-wrinkle Composition

This anti-wrinkle composition of the invention was obtained from the following ingredients:

| | |
|---|---|
| Tetraisopropyl orthotitanate | 20.2% |
| Polydimethylsiloxanediol | 27.7% |
| Diethoxydimethylsilane | 47.2% |
| Absolute ethanol | 8.0% |
| Water (pH = 1) | 0.9% |

This anti-wrinkle composition was produced by diluting the diethoxydimethylsilane in 80% of ethanol and then adding water brought to a pH of 1 (addition of hydrochloric acid) and stirring for about 1 minute.

Then the tetraisopropyl orthotitanate was added with stirring and finally the polydimethylsiloxanediol was added with stirring for about 30 minutes.

A fluid composition was thus obtained which, when applied in the form of a thin layer to the wrinkles surrounding the eyes, after evaporation of the volatile components led to the formation of a transparent and invisible film which had a tightening effect (pulling effect) thus perceptibly reducing the wrinkles surrounding the eyes.

Example 6

Fixing Composition for Hair

This composition was prepared as follows:

10.4 g of tetraethoxysilane were diluted in 2.3 g of ethanol and 2 g of deionized water and 2.5 ml of 1N HCl were then added. After stirring and homogenization, 3.85 g of a 30% alcoholic solution of a vinyl acetate/vinyl 4-tert-butylbenzoate/crotonic acid (65/25/10% by weight) copolymer with a GPC peak summit, molecular weight of 110,000 (described in FR-A-2 439 798) and neutralized by 2-amino-2-methylpropanol was added. 20 g of ethanol were added for a final dilution, and the mixture was stirred.

The final solution obtained was then packaged in a pump flask and sprayed onto the preshaped hair.

After drying, the hair was shiny, easy to disentangle and had good waviness.

Even after several washes using a shampoo consisting of 15% of sodium lauryl ether sulphate and 3% of cocoylbetaine and rinsing with water, the hair retained its initial shape and remained shiny.

What is claimed is:

1. Cosmetic or dermatological composition for forming a coating of a crosslinked hybrid material on a keratinous substrate, wherein said composition is a sol/gel type composition and is obtained by mixing:
    (a) at least one organometallic compound;
    (b) at least one functionalized organic polymer or a precursor of said polymer, or at least one functionalized silicone polymer or a precursor of said polymer, the latter precursor being different from (a);
    (c) a sufficient quantity of water to hydrolyse the organometallic compound; and
    (d) optionally, at least one alcohol; said coating being non reversible in nature.

2. Composition according to claim 1, wherein the organometallic compound is selected from the group consisting of:
    (i) organometallic oxides of transition metals from groups 1b to 7b, from the group 8 or from the lanthanide series in the periodic table;
    (ii) organometallic oxides of aluminum, boron, silicon, tin, titanium, cerium or tungsten; and (iii) organometallic phosphates.

3. Composition according to claim 1, wherein the organometallic compound is selected from the group consisting of:
(1) alkylsilanes, alkyl titanates or alkyl zirconates corresponding to one of the following formulae:

$$M(OR_1)_n \quad \text{(Ia)}$$

$$R-MO R(OR_1)_{n-1} \quad \text{(Ib)}$$

$$(OR_1)_{n-1}M-R-M(OR_1)_{n-1} \quad \text{(Ic)}$$

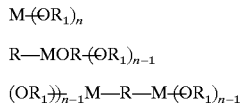   (Id)

where:
M represents Si, Ti or Zr;
n represents the valency of the metal;
$R_1$ represents a linear or branched $C_1$–$C_{30}$, alkyl radical;
R and R', independently of each other, represent a linear or branched alkyl radical, a cycloalkyl radical, a substituted or unsubstituted aryl radical, said radicals R and R' optionally being substituted by groups which are capable of reacting with the organic or silicone polymer and which can also contain a cosmetically or dermatologically active group; and
(2) chelated alkylsilanes, alkyl titanares or alkyl zirconates corresponding to the following formula:

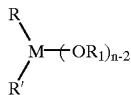   (II)

where:
$R_1$ and n have the meanings above for formulae (I)
b represents the degree of complexation of the ligand X;
x is the number of complexing ligands; and
X represents a mono- or polydentate chelating ligand or group which can be covalently bonded to a group which can react with the organic or silicone polymer said chelating group optionally also comprising a cosmetically or dermatologically active group.

4. Composition according to claim 3, wherein the chelated alkylsilanes, alkyl titanates or alkyl zirconates correspond to one of the following formulae:

$$M(OR_1)_{n-x}(X)_x \quad \text{(IIIa)}$$

$$R-M(OR_1)_{n-x}(X)_x \quad \text{(IIIb)}$$

$$(X)_x(OR_1)_{n-x}M-R-M(OR_1)_{n-x}(X)_x \quad \text{(IIIc)}$$

(IIId)

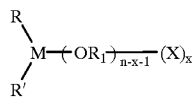

where:
X, R, R', $R_1$, n and x have the same meanings as those given above for formulae (I) and (II) in claim 3.

5. Composition according to claim 3, wherein the radicals R and R' are substituted by a group selected from ethyloni-cally unsaturated groups, halogenated groups, hydroxylated groups, carboxylated groups, thiol groups, epoxy groups, ester groups, amine groups, amino acid groups and polypeptide groups.

6. Composition according to claim 3, wherein the chelating group is covalently bonded to a group which can react with the organic or silicone polymer, selected from ethylenically unsaturated groups, halogenated groups, hydroxylated groups, carboxylated groups, thiol groups, epoxy groups. ester groups, amide groups, urethane groups and urea groups.

7. Composition according to claim 3, wherein said organic or silicone polymer is selected from amine groups, the acetoacetate (ACAC) group or a group derived from EDTA and its derivatives.

8. Composition according to claim 3, wherein the chelating group X is selected from the group consisting of carboxylic acids, β-ketones, β-diketones, β-keto esters, β-keto amines, α- and β-hydroxy acids, which may be β-hydroxylated, salicylic acid and derivatives thereof.

9. Composition according to claim 1, wherein the organometallic compound is selected from the group consisting of tetraethoxysilane, tetraisopropyl orthotitanate, tetrapropyl zirconate, methyltriethoxysilane, titanium tetraethoxide, titanium tetrabutoxide, iron triethoxide and tungsten triethoxide.

10. Composition according to claim 1, wherein the functionalized organic or silicone polymer is a random, block and/or graft polymer, and is selected from the group consisting of:
(a) homopolymers and copolymers of alkyloxazoline;
(b) homopolymers and copolymers of monomers selected from (meth)acrylic acid, crotonic acid, maleic acid, itaconic acid, styrenesulfonic acid, acrylamido-2-methyl-propane sulphonic acid, 2- sulphoethyl methacrylate, vinylsulphonic acid and vinylphosphonic acid;
(c) homopolymers of acrylic or methacrylic esters or amides and their copolymers with monomers selected from unsaturated carboxylic, sulphonic or phosphonic acids, vinyl esters or ethers, olefins, styrene, substituted styrenes, fluoro- or perfluoro-olefins, perfluoroalkyl (meth)acrylates, fluorinated vinyl compounds, and unsaturated organosilanes, organosiloxanes or organopoly-siloxanes;
(d) homopolymers and copolymers of vinyl alcohol;
(e) homopolymers of vinyl and/or allyl and/or methallyl esters or amides and their copolymers with monomers selected from the group consisting of unsaturated carboxylic, sulphonic or phosphonic acids, vinyl esters or ethers, olefins, styrene and substituted styrenes, fluoro- or perfluoro-olefins, perfluoroalkyl (meth) acrylates, fluorinated vinyl compounds, and unsaturated organosilanes, organosiloxanes or organopolysiloxanes;
(f) polyethers;
(g) polyesters;
(h) homo- and copolyolefins or cycloolefins;
(i) polyamides and polyesteramides;
(j) polyurethanes and polyureas which may comprise polyether, polyester and/or polyorganosiloxane sequences;
(k) fluorinated polymers;
(l) natural polymers and modified natural polymers;
(m) polyorganosiloxanes;

(n) polyorganophosphazines;

(o) polysilanes, polycarbosilanes or polysilazanes; and (p) mixtures thereof.

11. Composition according to claim 10, wherein the organic or silicone polymer is selected from the group consisting of poly(2-ethyl-2-oxazoline), the vinyl acetate/vinyl 4-tertbutyl-benzoate/crotonic acid (65/25/10%) copolymer, polydimethylsiloxanediols, polyethylene glycol, polyamyl alcohol and polyvinylpyrrolidone.

12. Composition according to claim 1, characterized in that the pH of the water is preferably in the range 1 to 12.

13. Composition according to claim 12, wherein the organometallic compound is an alkyl titanate or alkyl zirconate and the pH of the water is 3 or less.

14. Composition according to claim 1 wherein the alcohol is a linear or branched $C_1$–$C_6$ lower aliphatic alcohol.

15. Composition according to claim 1, wherein the weight ratio of the organometallic compound to the organic or silicone polymer is generally in the range from about 1:9.

16. Composition of claim 15 wherein said range is 8:2 to 2:8.

17. Composition according to claim 1, further comprising at least one cosmetically or dermatologically active ingredient selected from the group consisting of colorants, colored or colorless organic or mineral pigments, UV-A and/or UV-B sunscreens, enzymes, slimming agents, moisturizers, vitamins and α-hydroxy acids.

18. Composition according to claim 1, further comprising at least one usual cosmetic or dermatological additive.

19. Method for holding and/or coloring hair, comprising applying, by spraying onto the hair, a composition according to claim 1 and allowing the composition is to act until the solvent(s) has/have evaporated off.

20. Method according to claim 18 for coloring hair, wherein said composition contains at least one colorant and/or pigment.

21. Method according to claim 18, further comprising drying the hair after said solvent(s) have evaporated off.

22. Eyelash make-up method, comprising applying to the eyelashes, using a mascara brush, a sufficient quantity of a composition according to claim 1 and evaporating the solvent(s).

23. Method for making up or caring for the nails, comprising applying to the surface of the nail, using a brush, a layer of the composition according to claim 1 and then leaving the composition to act until the solvent(s) has/have evaporated off.

24. Method according to claim 21, wherein said composition contains at least one colorant and/or pigment.

25. Method for treating or caring for wrinkles on the skin, comprising applying to the parts of the skin to be treated a thin layer of a composition according to claim 1, and allowing the composition to act until the solvent(s) has/have evaporated off.

* * * * *